United States Patent [19]

Fannin et al.

[11] 4,299,781

[45] Nov. 10, 1981

[54] ORGANOMAGNESIUM SOLUTIONS OF LOW VISCOSITY

[75] Inventors: Loyd W. Fannin, Dickinson; Dennis B. Malpass, LaPorte, both of Tex.; Ramiro Sanchez, Vestal, N.Y.

[73] Assignee: Texas Alkyls, Inc., Deer Park, Tex.

[21] Appl. No.: 148,650

[22] Filed: May 12, 1980

[51] Int. Cl.$^3$ .............................................. C07F 3/02
[52] U.S. Cl. ........................... 260/665 R; 260/429 R
[58] Field of Search ....................... 260/665 R, 429 R

[56] References Cited

U.S. PATENT DOCUMENTS

| | | | |
|---|---|---|---|
| 3,452,111 | 6/1969 | Kamienski et al. | 260/665 R |
| 3,646,231 | 2/1972 | Kamienski et al. | 260/665 R |
| 3,755,478 | 8/1973 | Kamienski | 260/665 R |
| 4,069,267 | 1/1978 | Kamienski et al. | 260/665 R |
| 4,222,969 | 9/1980 | Fannin et al. | 260/665 R |

*Primary Examiner*—Helen M. S. Sneed
*Attorney, Agent, or Firm*—M. Henry Heines

[57] ABSTRACT

A low viscosity liquid solution is described, comprising
(a) a hydrocarbon-soluble dialkylmagnesium compound of 4 to 20 carbon atoms per molecule
(b) a solvent selected from the group consisting of aliphatic, alicyclic, and aromatic hydrocarbons of 5 to 20 carbon atoms, and
(c) an organometallic additive selected from the group consisting of $R_3Ga$, $R_3In$, and $RLi$, in which R is $C_1$–$C_{12}$ alkyl or $C_5$–$C_7$ cycloalkyl.

Also disclosed is a method of preparing such a solution by in situ generation of the dialkylmagnesium compound via the reaction between metallic magnesium and the appropriate alkyl halide in the presence of both the solvent and the organometallic additive.

23 Claims, No Drawings

ORGANOMAGNESIUM SOLUTIONS OF LOW VISCOSITY

BACKGROUND OF THE INVENTION

Organomagnesium compounds are known to be useful in a wide variety of chemical reactions. As reagents, organomagnesium compounds are used for the reduction of ketones, the metalation of aromatic compounds, and the alkylation of metal halides or oxides. As catalysts, organomagnesium compounds are useful in the dimerization and polymerization of olefins, see British Pat. No. 1,251,177, the polymerization of epoxides, see U.S. Pat. No. 3,444,102, and the preparation of telomers, see U.S. Pat. No. 3,742,077. While they perform many of the functions performed by Grignard reagents, organomagnesium compounds, owing to differences in electronic and steric factors, are more reactive toward certain types of compounds. For further discussion of organomagnesium reactions, the reader is referred to U.S. Pat. Nos. 3,646,231 and 3,822,219.

Some of the most useful organomagnesium compounds are dialkylmagnesium compounds. Although some are insoluble in hydrocarbon solvents, it has been shown that those containing branched-chain alkyl groups, cyclic alkyl groups, or straight-chain groups of five carbons or more are indeed soluble. Examples include di-tert-butylmagnesium, di-sec-butylmagnesium, di-n-amylmagnesium, methylisobutylmagnesium, ethylisobutylmagnesium, di-n-hexylmagnesium, dicyclohexylmagnesium, di-n-heptylmagnesium, etc. In addition, certain combinations of straight-chain lower alkyl groups have also been found to be soluble—n-butylethylmagnesium, n-butylmethylmagnesium, and n-propylmethylmagnesium.

Unfortunately, most of the resulting solutions are highly viscous. This detracts from the utility of the compounds since their viscosity renders them less reactive as reagents and catalysts and more difficult to handle and transfer. In addition, the viscosity of the solutions makes it difficult to prepare the compounds in a form free of halides and other undesirable solids. Following the procedure described in Glaze and Selman, *Journal of Organometallic Chemistry*, Vol. 5, p. 477, (1967), and W. N. Smith, *Journal of Organometallic Chemistry*, Vol. 64, p. 25 (1974), dialkylmagnesium compounds are conveniently prepared by the reaction between metallic magnesium and the appropriate alkyl chloride in the desired hydrocarbon solvent. The by-product of this reaction is magnesium chloride, which is insoluble in hydrocarbons. Both the magnesium chloride and any unreacted magnesium metal, which is frequently used in excess, remain as solid matter suspended in a viscous liquid. The viscosity prevents an easy separation of the solution from the solids, requiring instead centrifuging equipment or the like or a long period for the solids to settle.

SUMMARY OF THE INVENTION

It has now been discovered that a substantial reduction in the viscosity of hydrocarbon solutions of dialkylmagnesium compounds is achieved by the inclusion of organometallic compounds of gallium, indium, or lithium in the solution.

Specifically, this invention resides in a low viscosity liquid solution comprising (a) a hydrocarbon-soluble dialkylmagnesium compound of 4 to 20 carbon atoms per molecule, (b) a solvent selected from the group consisting of aliphatic, alicyclic, and aromatic hydrocarbons of 5 to 20 carbon atoms, and (c) an organometallic additive selected from $R_3Ga$, $R_3In$, and $RLi$, in which R is $C_1-C_{12}$ alkyl or $C_5-C_7$ cycloalkyl.

This invention also resides in a process for the preparation of the hydrocarbon solution described above by reaction between metallic magnesium and the appropriate alkyl halide in the presence of both the desired solvent and the organometallic compound. The lowered viscosity of the resulting solution greatly facilitates this process. Other aspects of this invention will be apparent from the following description.

DETAILED DESCRIPTION OF THE INVENTION

The three basic components of the instant composition are a hydrocarbon-soluble dialkylmagnesium compound, a hydrocarbon solvent, and an organometallic compound of gallium, indium, or lithium. For a further understanding of this invention, each of these components will be discussed in both its broad and preferred aspects.

The dialkylmagnesium compound is any such compound of 4 to 20 carbon atoms per molecule which is known to have substantial solubility in hydrocarbon solvents. This includes magnesium alkyls where at least one of the two groups attached to the magnesium atom is a branched-chain alkyl group, a cyclic alkyl group, or a straight-chain alkyl group of five carbon atoms or more. The two groups can either be the same or different as long as this condition is met. Examples of dialkylmagnesium compounds falling under this description include methylisobutylmagnesium, ethylisobutylmagnesium, di-n-amylmagnesium, n-butyl-n-hexylmagnesium, ethyl-n-hexylmagnesium, di-n-hexylmagnesium, dicyclohexylmagnesium, di-n-heptylmagnesium, etc. The dialkylmagnesium compounds of the present composition also include those in which the two alkyl groups are unbranched with less than five carbon atoms apiece but differ in length by at least two carbon atoms—i.e., n-butylethylmagnesium, n-butylmethylmagnesium, and n-propylmethylmagnesium—since these are also known to be soluble in hydrocarbons. As this description indicates, the "alkyl" portion of the term "dialkylmagnesium compound" is intended to include straight-chain, branched-chain, and cyclic groups, and the range of 4 to 20 carbon atoms represents the total of the two groups on each magnesium atom. Dialkylmagnesium compounds within the range of 5 to 15 carbon atoms are preferred. All carbon atom ranges in this specification are inclusive of upper and lower limits.

The concentration of the dialkylmagnesium compound in the solvent is not critical and can vary over a wide range. In many cases, the solubility of the compound is increased by the inclusion of the organometallic compound. In general, however, viscosity increases with concentration. The preferred concentration, therefore, is from about 0.2% to about 50.0% dialkylmagnesium compound by weight, most preferably from about 1.0 to about 25.0% by weight.

The term "hydrocarbon solvent" is used herein to designate aliphatic, alicyclic, and aromatic hydrocarbons. Illustrative of aliphatic solvents are n-pentane, iso-pentane, n-hexane, n-heptane, n-octane, isooctane, pentamethylheptane, and gasoline and other petroleum fractions. Illustrative of alicyclic solvents are cyclopentane, cyclohexane, methylcyclohexane, methylcyclopentane, cycloheptane, and cyclooctane. Illustrative of aromatic solvents are benzene, toluene, xylene, ethylbenzene, tetralin, and α-methylnaphthalene. Preferred solvents are those containing 5 to 20 carbon atoms. More preferred are those containing 6 to 15 carbon atoms.

The term "organometallic compound" is used herein to designate the viscosity reducing agent, and represents an alkylated compound of gallium, indium, or lithium according to the following formulae:

in which R is $C_1$–$C_{12}$ alkyl or $C_5$–$C_7$ cycloalkyl. The three groups in either the gallium or indium compounds can be the same or different. Preferably, all alkyl groups on the molecule are the same and R is $C_1$–$C_6$ alkyl. The term "alkyl" as used in defining the organometallic compound includes both straight-chain and branched-chain groups. Examples of organometallic compounds within the scope of this invention are trimethylgallium, triethylgallium, tri-n-propylgallium, triisobutylgallium, n-butyldiethylgallium, n-hexyldimethylgallium, tri-n-hexylgallium, trimethylindium, triethylindium, tri-n-butylindium, tri-sec-butylindium, n-propyllithium, n-butyllithium, tert-butyllithium, sec-butyllithium, n-amyllithium, n-hexyllithium, etc. Organometallic compounds which are normally insoluble in the hydrocarbon solvent are as useful as those which are normally soluble since the dialkylmagnesium compound has a solubilizing effect, bringing insoluble organometallics into solution.

The organometallic compound can be added as such to the solution or generated in situ from a halide precursor. Typical precursors are $GaX_3$, $InX_3$, or $LiX$, in which X is chlorine, bromine, or iodine; preferably chlorine or bromine; most preferably chlorine. When added to the solution, the precursor undergoes an exchange reaction with the dialkylmagnesium compound whereby the halogens are replaced with alkyl groups and magnesium halide precipitates out of solution. The solids are then easily removed to leave a low viscosity solution.

The quantity of organometallic compound in the present composition is not critical and can vary over a wide range, since very little is required to produce a marked decrease in the solution viscosity. In general, however, it will be most convenient and economical to use a quantity such that the mole ratio of the organometallic compound to the dialkylmagnesium compound is from about 0.001:1 to about 0.25:1, preferably from about 0.001:1 to about 0.10:1, and most preferably from about 0.01:1 to about 0.05:1.

The solution can easily be prepared by physically combining the three basic components. Solubilization can be hastened by moderate heating of the resulting mixture and/or agitation. The resulting solution is clear and the compounds will remain in solution upon subsequent lowering of the temperature.

The dialkylmagnesium compound itself can be prepared by any of the several known techniques. One such technique is the mercury-magnesium exchange method as disclosed in Cowan and Mosher, *Journal of Organic Chemistry*, Vol. 27, p. 1 (1962), which involves the following reaction:

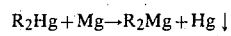

where R is alkyl. Mercury precipitates from the solution as a by-product and is thus readily removed.

Another technique is the dioxanate precipitation method, as disclosed in Schlenk, *Berichte der Deutschen Chemischen Gesselschaft*, Vol. 64, p. 734 (1931). In this method, the following reaction occurs:

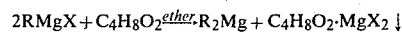

where R is alkyl and X is halogen. The precipitated complex is then removed from the solution by filtration to leave an etherated dialkylmagnesium complex from which the ether must be removed prior to use of the dialkylmagnesium compound in the present composition.

A third method is the reaction of an alkyllithium compound with a magnesium halide as described in U.S. Pat. No. 3,646,231:

where R is alkyl and X is halogen. Again, the precipitated lithium halide must be removed from the solution. Other preparative techniques will be apparent to those skilled in the art.

The preferred technique involves the reaction between metallic magnesium and the appropriate alkyl halide. If an alkylmagnesium compound with two different alkyl groups is desired, the two alkyl halides are used either simultaneously or in succession and a product with mixed alkyl groups is achieved by alkyl interchange. The solvent and organometallic additive can be added before, during, or after the reaction, and the precipitated or remaining solids are then removed by filtration. The organometallic additive greatly simplifies the solids removal step since, by lowering the solution viscosity, the organometallic additive promotes faster settling of the solids.

In this reaction, commercial grade magnesium turnings or shavings can be used. It is preferable, however, to use higher surface area forms of the metal. While the surface area can be increased by milling, the use of finely divided magnesium powder is most preferred, with a particle size equal to or less than about 500 microns. This form of the metal serves to enhance the reaction rate and minimize the occurrence of Wurtz coupling reactions.

The alkyl halides used in this reaction can be chlorides, bromides, iodides, or combinations thereof. Chlorides are generally preferred for reasons of economy. Usually, a small amount of halide is present in the final product solution. This can be minimized by the use of chlorides rather than iodides or bromides, since the amount of soluble halide observed decreases in the order I > Br > Cl.

The reactant mole ratio can be varied over a wide range since there is no critical range with regard to reaction rate or product yield. Normally, however, the starting materials will be such that the mole ratio of magnesium to alkyl halide is from about 1.0 to about 2.0, preferably from about 1.1 to about 1.3. The excess magnesium inherent in mole ratios greater than 1.0 is effective in minimizing Wurtz coupling reactions.

The reactivity of the alkyl halides increases with increasing chain length. Thus, methyl and ethyl halides are rather slow to react and frequently require the use of a magnesium activating agent to initiate the reaction. The term "magnesium activating agent" is used herein to denote heat or any substance which, when contacted with magnesium, will cause the reaction to occur at a substantially faster rate. Many activating agents are known in the art. Typical examples are $AlCl_3$, $AlCl_3$-ether complexes, N,N-dimethylaniline, molecular iodine, Grignard reagents, and dialkylmagnesium compounds or alkyl halides of higher chain length. Thus, since methyl and ethyl halides will be used only in conjunction with higher alkyl halides, a small amount of the latter is effective in initiating the reaction. Thermal activation is generally achieved at temperatures between about 125° C. and about 350° C., preferably from about 150° C. to about 250° C. At least 10% by weight of methyl or ethyl halide based on the weight of magnesium metal must be present during thermal activation.

Once the reaction has been initiated, it can proceed at lower temperatures and can occur over a wide temperature range. It will be most convenient, however, to operate between about 50° C. and about 200° C., preferably between about 80° C. and about 150° C. These temperatures are not critical and are dictated largely by practical considerations such as process economics, energy conservation, and the possibility of alkyl halide decomposition at high temperatures.

The reaction pressure is not critical and can range from atmospheric pressure to elevated pressures of several atmospheres. When low molecular weight halides are used, the reaction will be most conveniently run at a pressure in slight excess of atmospheric in order to keep the alkyl halide in solution. Elevated pressures are not necessary with longer chain lengths.

Magnesium alkyls are pyrophoric substances, capable of spontaneous ignition upon contact with air. To prevent such ignition, and also to prevent oxidation of the metallic magnesium, the reaction must be carried out in the absence of more than trace amounts of oxygen. The reaction is normally carried out in an atmosphere of inert gas such as nitrogen or argon, or in an atmosphere of alkyl halide gas, when a highly volatile alkyl halide is used. The reaction must also be conducted in the substantial absence of water, due to the susceptibility of the system components to decomposition in the presence of water.

The following examples are offered as further illustration of the present invention. They are intended neither to define nor to limit the invention in any manner.

EXAMPLE 1

This example demonstrates the ability of trimethylgallium to reduce the viscosity of a heptane solution of n-butylethylmagnesium, a hydrocarbon-soluble organomagnesium compound. The viscosity reduction is used in this example to facilitate the separation of the solution from solids which remain in suspension following the in situ preparation of n-butylethylmagnesium in the solvent.

An aerosol compatibility test bottle reactor was charged with 9.0 g (0.370 g-atom) of 100-mesh magnesium powder and placed in an oil heating bath at 160° C. The reactor was then purged with ethyl chloride gas and allowed to reach thermal equilibrium at a pressure of 8.5 pounds per square inch gauge (5.9 Newtons/cm$^2$). The bath was then cooled to 105° C. and the reactor was charged with 201 g of commercial heptane solvent (approximately 75% n-heptane, remainder primarily isoheptanes). Additional ethyl chloride was then fed with stirring over a period of about 1.5 hours until a total of 10.1 g (0.158 mole) of ethyl chloride had been added. The bath was then cooled to 80° C. and 13.2 g (0.143 mole) of n-butyl chloride was added with stirring over a period of about 1 hour.

The result was a thick slurry of suspended solids including magnesium chloride and unreacted magnesium metal. A sample of the liquid phase was extracted from the slurry for analysis, which indicated 0.10% chloride and 1.28% magnesium by weight. The latter is equivalent to 5.82% n-butylethylmagnesium by weight.

The slurry was then set aside to allow the solids to settle at room temperature. Settling was permitted to occur gradually over a period of 45 hours. Although settling after 45 hours was incomplete, the solids level at the bottom of the container was noted.

After the solids level was noted, the container was manually shaken to convert the mixture back to its original form as a thick slurry. Trimethylgallium was then added to the slurry to give an Mg/Ga atomic ratio of 100, and the slurry was again set aside to permit settling of the solids. The solution was obviously less viscous, and after one hour, it was observed that the solids had settled to an even greater degree than they had after 45 hours without the trimethylgallium present. Clearly, the presence of the trimethylgallium had substantially lowered the viscosity of the solution, permitting settling to occur at a much faster rate.

EXAMPLE 2

This example demonstrates the effectiveness of a variety of organometallic additives within the scope of the present invention in reducing the viscosity of a heptane solution of n-butylethylmagnesium.

A solution containing 9.8% n-butylethylmagnesium by weight in n-heptane was used to test the various additives. Viscosity measurements were taken on a modified Ostwald viscometer at 30° C. The results are shown in Table I, where the solution in the absence of any additive shows a viscosity of 1343 centipoise, which is much higher than any of the additive-containing solutions.

TABLE I

EFFECT OF ADDITIVES ON VISCOSITY OF 9.8% n-$C_4H_9MgC_2H_5$ SOLUTION IN n-HEPTANE

| Additive | Mole % Additive Relative to n-$C_4H_9MgC_2H_5$ | Viscosity at 30° C. (centipoise) |
|---|---|---|
| No additive present | | 1343 |
| Ga(CH$_3$)$_3$ | 3.39 | 8.8 |
| In(CH$_2$H$_5$)$_3$ | 3.98 | 26.0 |
| InCl$_3$ | 3* | <50* |
| t-C$_4$H$_8$Li | 4.03 | 373.0 |
| t-C$_4$H$_8$Li | 3.68 | 9.7 |

*The test on indium trichloride was qualitative and the viscosity for this test is an estimated value.

EXAMPLE 3

This example demonstrates the viscosity reduction of a heptane solution of di-n-hexylmagnesium with the use of trimethylgallium.

To prepare the solution, a ten-gallon (37.9 liter) reactor was charged with 11.4 kg of n-heptane, 1.0 kg of 100-mesh magnesium powder, and 0.116 kg of preformed di-n-hexylmagnesium (to help initiate the reaction). The reactor contents were heated to 110° C. under a nitrogen atmosphere, and 4.15 kg of n-hexyl chloride was slowly added over a period of one hour. After the reaction was complete, the solids were allowed to settle while the 110° C. temperature was maintained without agitation. The solids were then removed and the viscous liquid was analyzed to indicate 2.02 weight percent magnesium, equivalent to 16.2 weight percent di-n-hexylmagnesium in solution. The viscosity of the solution was 3280 centipoise.

Trimethylgallium was then added to a portion of the viscous solution at a quantity to produce an Mg/Ga atomic ratio of 120. From visual observation and manual swirling of the solution, it was apparent that the viscosity was immediately reduced to less than 100 centipoise (in comparison with similar solutions where viscosity had been measured).

EXAMPLE 4

This example demonstrates the in situ formation of tri-n-hexylgallium as a viscosity reducer for an n-heptane solution of di-n-hexylmagnesium.

A second sample of the n-heptane solution of di-n-hexylmagnesium described in Example 3 was used for this test. Here, however, the precursor gallium trichloride was added to the solution at an Mg/Ga atomic ratio of about 6. This time, from observation and swirling, it was apparent that the resulting solution had a viscosity which was about the same as that of n-heptane alone, i.e., less than 10 centipoise.

What is claimed is:
1. A low viscosity liquid solution comprising
(a) a hydrocarbon-soluble dialkylmagnesium compound of 4 to 20 carbon atoms per molecule at a concentration of from about 0.2% to about 50% by weight,
(b) a solvent selected from the group consisting of aliphatic, alicyclic, and aromatic hydrocarbons of 5 to 20 carbon atoms, and
(c) an organometallic additive selected from the group consisting of $R_3Ga$, $R_3In$, and $RLi$, in which R is $C_1$–$C_{12}$ alkyl or $C_5$–$C_7$ cycloalkyl, at a mole ratio of from about 0.001:1 to about 0.25:1 with respect to the dialkylmagnesium compound.

2. A low viscosity solution according to claim 1 in which the dialkylmagnesium compound contains from 5 to 15 carbon atoms per molecule.

3. A low viscosity solution according to claim 1 in which the concentration of dialkylmagnesium compound is from about 1.0% to about 25.0% by weight.

4. A low viscosity solution according to claim 1 in which the solvent is selected from the group consisting of aliphatic, alicyclic, and aromatic hydrocarbons of 6 to 15 carbon atoms.

5. A low viscosity solution according to claim 1 in which the organometallic additive is selected from the group consisting of $R_3Ga$, $R_3In$, and $RLi$, in which R is $C_1$–$C_6$ alkyl.

6. A low viscosity solution according to claim 1 in which the organometallic additive is generated in situ from the corresponding metallic halide selected from the group consisting of $GaX_3$, $InX_3$, and $LiX$, where X is selected from the group consisting of chlorine, bromine, and iodine.

7. A low viscosity solution according to claim 1 in which the organometallic additive is trimethylgallium.

8. A low viscosity solution according to claim 1 in which the organometallic additive is generated in situ from gallium trichloride.

9. A low viscosity solution according to claim 1 in which the organometallic additive is present at a mole ratio of from about 0.001:1 to about 0.10:1 with respect to the dialkylmagnesium compound.

10. A low viscosity solution according to claim 1 in which the organometallic additive is present at a mole ratio of from about 0.01:1 to about 0.05:1 with respect to the dialkylmagnesium compound.

11. A process for the manufacture of hydrocarbon solution of a dialkylmagnesium compound which comprises
(a) reacting metallic magnesium with at least one alkyl halide selected to produce a hydrocarbon-soluble dialkylmagnesium compound of 4 to 20 carbon atoms per molecule, in the presence of or followed by the addition of a hydrocarbon solvent and an organometallic additive selected from the group consisting of $R_3Ga$, $R_3In$, and $RLi$, in which R is $C_1$–$C_{12}$ alkyl or $C_5$–$C_7$ cycloalkyl, such that the concentration of dialkylmagnesium compound is from about 0.2% to about 50% by weight, and the mole ratio of organometallic additive to dialkylmagnesium compound is from about 0.001:1 to about 0.25:1, to produce a homogeneous liquid and solids, and
(b) separating said homogeneous liquid from said solids, both steps being conducted in the substantial absence of both moisture and oxygen.

12. A process according to claim 11 in which the dialkylmagnesium compound contains from 5 to 15 carbon atoms per molecule.

13. A process according to claim 11 in which the solvent is selected from the group consisting of aliphatic, alicyclic and aromatic hydrocarbons of 6 to 15 carbon atoms.

14. A process according to claim 11 in which the organometallic additive is selected from the group consisting of $R_3Ga$, $R_3In$, and $RLi$, in which R is $C_1$–$C_6$ alkyl.

15. A process according to claim 11 in which the organometallic additive is present at a mole ratio of from about 0.001:1 to about 0.10:1 with respect to the dialkylmagnesium compound.

16. A process according to claim 11 in which the organometallic additive is present at a mole ratio of from about 0.01:1 to about 0.05:1 with respect to the dialkylmagnesium compound.

17. A process according to claim 11 in which the metallic magnesium is comprised of particles equal to or less than 500 microns in diameter.

18. A process according to claim 11 in which the mole ratio of magnesium to alkyl halide is from about 1.0 to about 2.0.

19. A process according to claim 11 in which the mole ratio of magnesium to alkyl halide is from about 1.1 to about 1.3.

20. A process according to claim 11 in which the alkyl halide is an alkyl chloride.

21. A process according to claim 11 in which the organometallic additive is generated in situ from the corresponding metallic halide selected from the group consisting of $GaX_3$, $InX_3$, and $LiX$, where X is selected from the group consisting of chlorine, bromine, and iodine.

22. A process according to claim 11 in which the organometallic additive is trimethylgallium.

23. A process according to claim 11 in which the organometallic additive is generated in situ from gallium trichloride.

* * * * *

UNITED STATES PATENT AND TRADEMARK OFFICE
CERTIFICATE OF CORRECTION

PATENT NO. : 4,299,781
DATED : May 12, 1981
INVENTOR(S) : Loyd W. Fannin et al.

It is certified that error appears in the above—identified patent and that said Letters Patent is hereby corrected as shown below:

In Column 6, at Table I, the third entry in the "Additive" column should read --- $In(C_2H_5)_3$ ---.

In Column 6, at Table I, the fifth entry in the "Additive" column should read -- $N-C_4H_9Li$ --.

Signed and Sealed this

Sixth Day of July 1982

[SEAL]

Attest:

Attesting Officer

GERALD J. MOSSINGHOFF
Commissioner of Patents and Trademarks